United States Patent
Kuechler et al.

(10) Patent No.: US 9,475,745 B2
(45) Date of Patent: *Oct. 25, 2016

(54) PROCESS FOR PRODUCING PHENOL

(71) Applicant: ExxonMobil Chemical Patents Inc., Baytown, TX (US)

(72) Inventors: Keith H. Kuechler, Friendswood, TX (US); Charles Morris Smith, Princeton, NJ (US); Francisco M. Benitez, Cypress, TX (US); Kun Wang, Bridgewater, NJ (US); Hari Nair, Houston, TX (US); Travis A. Reine, Slidell, LA (US); Gabor Kiss, Hampton, NJ (US); Roberto Garcia, Easton, PA (US); Christopher L. Becker, Manhattan, KS (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/433,211

(22) PCT Filed: Nov. 13, 2013

(86) PCT No.: PCT/US2013/069846
§ 371 (c)(1),
(2) Date: Apr. 2, 2015

(87) PCT Pub. No.: WO2014/081597
PCT Pub. Date: May 30, 2014

(65) Prior Publication Data
US 2015/0251986 A1 Sep. 10, 2015

Related U.S. Application Data

(60) Provisional application No. 61/729,019, filed on Nov. 21, 2012.

(30) Foreign Application Priority Data

Feb. 1, 2013 (EP) ..................................... 13153675

(51) Int. Cl.
C07C 45/00 (2006.01)
C07C 37/00 (2006.01)
C07C 45/53 (2006.01)
C07C 37/08 (2006.01)
C07C 2/74 (2006.01)
C07C 407/00 (2006.01)

(52) U.S. Cl.
CPC ................. *C07C 45/53* (2013.01); *C07C 2/74* (2013.01); *C07C 37/08* (2013.01); *C07C 407/00* (2013.01); *C07C 2101/14* (2013.01)

(58) Field of Classification Search
CPC ....... C07C 45/53; C07C 407/00; C07C 2/74; C07C 37/08; C07C 49/403; C07C 13/28; C07C 39/04; C07C 409/14; C07C 2101/14
USPC .................................................. 568/361, 800
See application file for complete search history.

(56) References Cited

U.S. PATENT DOCUMENTS

| | | | |
|---|---|---|---|
| 4,016,213 A | 4/1977 | Yeh et al. | |
| 4,021,490 A | 5/1977 | Hudson | |
| 6,037,513 A | 3/2000 | Chang et al. | |

FOREIGN PATENT DOCUMENTS

| | | |
|---|---|---|
| WO | WO 2012/067711 | 5/2012 |
| WO | WO 2012/145029 | 10/2012 |
| WO | WO 2012/145032 | 10/2012 |

*Primary Examiner* — Jafar Parsa
(74) *Attorney, Agent, or Firm* — Siwen Chen; Stephen A. Baehl

(57) ABSTRACT

In a process for producing phenol and cyclohexanone, a cleavage feed containing greater than 40 wt % and no greater than 95 wt % cyclohexyl-1-phenyl-1-hydroperoxide, and at least 5 wt % and less than 60 wt % cyclohexylbenzene is mixed with at least phenol, cyclohexanone, water, and sulfuric acid to produce a cleavage reaction mixture containing from 15 wt % to 50 wt % phenol, from 15 wt % to 50 wt % cyclohexanone, from 1 wt % to 10 wt % cyclohexyl-1-phenyl-1-hydroperoxide, from 5 wt % to 60 wt % cyclohexylbenzene, from 0.1 wt % to 4 wt % water, and from 10 wppm to 1000 wppm sulfuric acid. The cleavage reaction mixture is then reacted at a temperature from 30° C. and to 70° C., and a pressure of at least 1 atmosphere for a time sufficient to convert at least 50% of said cyclohexyl-1-phenyl-1-hydroperoxide in said cleavage reaction mixture and produce a cleavage effluent containing phenol and cyclohexanone.

25 Claims, 2 Drawing Sheets

PROCESS FOR PRODUCING PHENOL

PRIORITY CLAIM TO RELATED APPLICATIONS

This application is a National Stage Application of International Application No. PCT/US2013/069846 filed Nov. 13, 2013, which claims priority to U.S. Provisional Application Ser. No. 61/729,019 filed Nov. 21, 2012, and European Application No. 13153675.7 filed Feb. 1, 2013, the disclosures of which are fully incorporated herein by their reference.

FIELD

The present invention relates to a process for producing phenol.

BACKGROUND

Phenol is an important product in the chemical industry and is useful in, for example, the production of phenolic resins, bisphenol A, ε-caprolactam, adipic acid, and plasticizers.

Currently, the most common route for the production of phenol is the Hock process via cumene. This is a three-step process in which the first step involves alkylation of benzene with propylene in the presence of an acidic catalyst to produce cumene. The second step is oxidation, preferably aerobic oxidation, of the cumene to the corresponding cumene hydroperoxide. The third step is the cleavage of the cumene hydroperoxide in the presence of heterogeneous or homogeneous catalysts into equimolar amounts of phenol and acetone, a co-product. However, the world demand for phenol is growing more rapidly than that for the acetone co-product. In addition, due to developing shortages in supply, the cost of propylene is likely to increase.

Thus, a process that avoids or reduces the use of propylene as a feed and coproduces higher ketones, rather than acetone, may be an attractive alternative route to the production of phenol. For example, there is a growing market for cyclohexanone, which is used as an industrial solvent, as an activator in oxidation reactions and in the production of adipic acid, cyclohexanone resins, cyclohexanone oxime, caprolactam, and nylon 6.

It is known that phenol and cyclohexanone can be co-produced by a variation of the Hock process in which cyclohexylbenzene is oxidized to obtain cyclohexylbenzene hydroperoxide and the hydroperoxide is decomposed in the presence of an acid catalyst to the desired phenol and cyclohexanone. Although various methods are available for the production of cyclohexylbenzene, a preferred route is disclosed in U.S. Pat. No. 6,037,513, which discloses that cyclohexylbenzene can be produced by contacting benzene with hydrogen in the presence of a bifunctional catalyst comprising a molecular sieve of the MCM-22 family and at least one hydrogenation metal selected from palladium, ruthenium, nickel, cobalt, and mixtures thereof. The '513 patent also discloses that the resultant cyclohexylbenzene can be oxidized to the corresponding hydroperoxide which is then decomposed to the desired phenol and cyclohexanone co-product.

Although the production of phenol and cyclohexanone from cyclohexylbenzene appears to be analogous to the Hock process for producing phenol and acetone from cumene, the chemistries in each step are actually very different. For example, the chemistry of the cleavage of cyclohexylbenzene hydroperoxide is much more complicated than that for cumene hydroperoxide and more by-products (both in types and amounts) can form. Thus, cleavage of cyclohexylbenzene hydroperoxide to phenol and cyclohexanone is acid catalyzed and, although a variety of acid catalysts can be used, sulfuric acid is preferred for its low cost and easy availability. However, significant yield loss to by-product (both primary and secondary) can occur in the sulfuric acid-based cleavage of cyclohexylbenzene hydroperoxide. Primary by-products may include the β-scission products such as hexanophenone and 6-hydroxyl-hexanophenone (6-HHP). Examples of secondary by-products include those derived from cyclohexanone, such as 2-(1-cyclohexenyl)cylohexanone and 2-(cyclohexylidene) cyclohexanone (cyclohexanone aldol condensation products), 2-hydroxycyclohexanone and cyclohexenone (cyclohexanone oxidation products). Formation of the primary by-products result in loss of both phenol and cyclohexanone; while secondary by-products further reduce yield to cyclohexanone.

SUMMARY

There is therefore significant interest in developing a sulfuric acid catalyzed process for the cleavage of cyclohexylbenzene hydroperoxide in which the yield of phenol and cyclohexanone is maximized. According to the present disclosure, it has now been found that an optimized composition of the cleavage reaction medium is particularly conducive to achieving high yields of both phenol and cyclohexanone in the conversion of cyclohexylbenzene hydroperoxide in the presence of a sulfuric acid catalyst. In addition, since the cleavage reaction does not achieve 100% conversion in a single pass, recycle of part of the cleavage effluent is desired for a higher overall conversion. Moreover, it has been found that the cleavage recycle stream provides an effective vehicle for controlling the composition of the cleavage reaction medium.

Accordingly, the present disclosure resides in one aspect in a process for producing phenol and cyclohexanone, the process comprising:

(a) providing a cleavage feed containing greater than 40 wt % and no greater than 95 wt % cyclohexyl-1-phenyl-1-hydroperoxide, and at least 5 wt % and less than 60 wt % cyclohexylbenzene;

(b) mixing said cleavage feed with at least phenol, cyclohexanone, water, and sulfuric acid, to produce a cleavage reaction mixture containing from 15 wt % to 50 wt % phenol, from 15 wt % to 50 wt % cyclohexanone, from 1 wt % to 10 wt % cyclohexyl-1-phenyl-1-hydroperoxide, from 5 wt % to 60 wt % cyclohexylbenzene, from 0.1 wt % to 4 wt % water, and from 10 wppm to 1000 wppm sulfuric acid; and (c) reacting said cleavage reaction mixture at a temperature from 30° C. and to 70° C. for a time sufficient to convert at least 50% of said cyclohexyl-1-phenyl-1-hydroperoxide in said cleavage reaction mixture and produce a cleavage effluent containing phenol and cyclohexanone.

The process may further include:

(d) dividing said cleavage effluent into at least a cleavage product and a cleavage recycle, wherein said cleavage recycle provides at least a portion of said phenol, cyclohexanone, water, and sulfuric acid mixed with said cleavage feed in step (b).

In a further aspect, the present disclosure resides in a process for producing phenol and cyclohexanone, the process comprising:

(a) providing a cleavage feed containing cyclohexyl-1-phenyl-1-hydroperoxide;

(b) mixing said cleavage feed with at least phenol and cyclohexanone to produce a cleavage reaction mixture; and (c) reacting said cleavage reaction mixture in the presence of a sulfuric acid catalyst under conditions to maintain the weight ratio of phenol to cyclohexanone in said cleavage reaction mixture in excess of 1:1 and to convert part of said cyclohexyl-1-phenyl-1-hydroperoxide in said cleavage reaction mixture and produce a cleavage effluent containing phenol and cyclohexanone.

In yet a further aspect, the present disclosure resides in a process for producing phenol and cyclohexanone, the process comprising:

(a) hydroalkylating benzene with hydrogen in the presence of a first catalyst under conditions effective to produce a hydroalkylation product comprising cyclohexylbenzene;

(b) contacting at least part of said cyclohexylbenzene with an oxygen-containing compound in the presence of a second catalyst under oxidation conditions effective to produce an oxidation product comprising cyclohexyl-1-phenyl-1-hydroperoxide and unreacted cyclohexylbenzene;

(c) providing from said oxidation product a cleavage feed containing greater than 40 wt % and no greater than 95 wt % cyclohexyl-1-phenyl-1-hydroperoxide, and at least 5 wt % and less than 60 wt % cyclohexylbenzene;

(d) mixing said cleavage feed with at least phenol, cyclohexanone, water, and sulfuric acid, to produce a cleavage reaction mixture containing from 15 wt % to 50 wt % phenol, from 15 wt % to 50 wt % cyclohexanone, from 1 wt % to 10 wt % cyclohexyl-1-phenyl-1-hydroperoxide, from 5 wt % to 60 wt % cyclohexylbenzene, from 0.1 wt % to 4 wt % water, and from 10 wppm to 1000 wppm sulfuric acid; and (e) reacting said cleavage reaction mixture at a temperature from 30° C. and to 70° C. for a time sufficient to convert at least 50% of said cyclohexyl-1-phenyl-1-hydroperoxide in said cleavage reaction mixture and produce a cleavage effluent containing phenol and cyclohexanone.

DETAILED DESCRIPTION OF THE EMBODIMENTS

Figure 1:
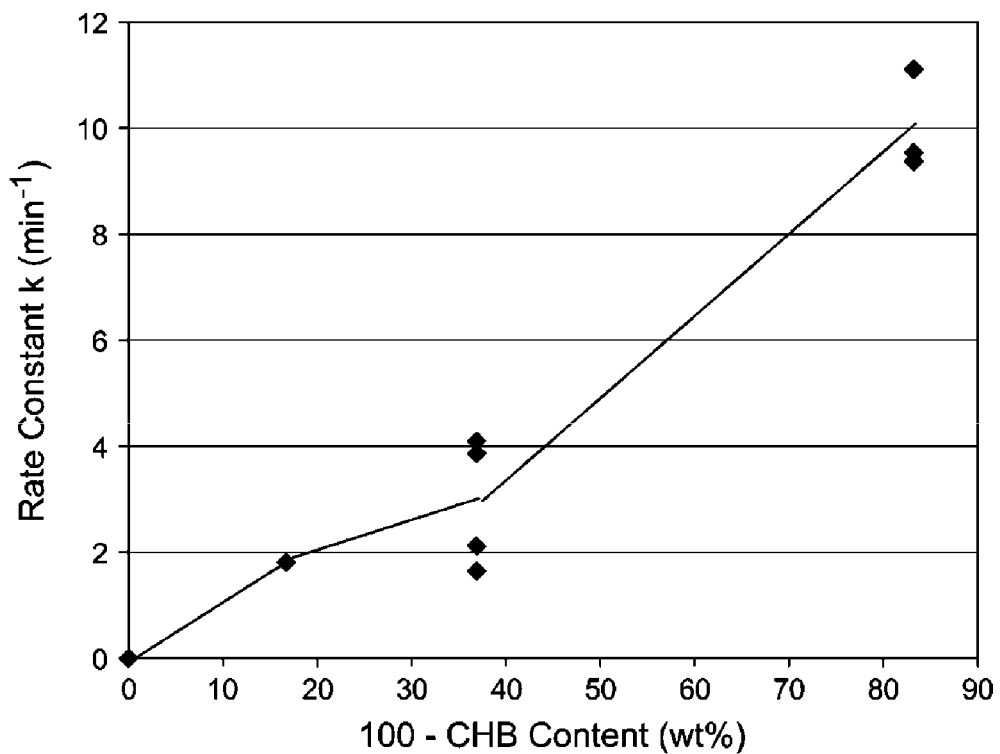
FIG. 1 is a graph of first order rate constant against the sum of all components other than cyclohexylbenzene (CHB) in the reaction mixtures employed in the process of Example 1.

In the present disclosure, a process may be described as comprising at least one "step." It should be understood that each step is an action or operation that may be carried out once or multiple times in the process, in a continuous or discontinuous fashion. Unless specified to the contrary, or the context clearly indicates otherwise, each step in a process may be conducted sequentially in the order as they are listed, with or without overlapping with one or more other step, or in any other order, as the case may be. In addition, some steps may be conducted simultaneously, for example, in the same reaction zone. Preferably, however, the steps are performed in the order listed.

Unless otherwise indicated, all numbers in the present disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contain a certain level of error due to the limitation of the technique and equipment used for making the measurement.

As used herein, the indefinite article "a" or "an" shall mean "at least one" unless specified to the contrary or the context clearly indicates otherwise. Thus, embodiments using "a hydrogenating metal" include embodiments where one, two or more hydrogenating metals are used, unless specified to the contrary or the context clearly indicates that only one hydrogenating metal is used. Likewise, "an oxygenated hydrocarbon" should be interpreted to include one or more types of hydrogenated hydrocarbon at various concentrations unless specified or indicated by the context to mean only one specific type of hydrogenated hydrocarbon.

As used herein, the term "cyclohexylbenzene" shall mean benzene substituted by a single cyclohexyl group, unless specified to the contrary or the context clearly indicates otherwise. As used herein, the generic term "dicyclohexylbenzene" shall include 1,2-dicyclohexylbenzene, 1,3-dicyclohexylbenzne, 1,4-dicyclohexylbenzene, and mixtures and combinations of at least two thereof in any proportion. As used herein, the generic term "tricyclohexylbenzene" shall include 1,2,3-tricyclohexylbenzene, 1,2,4-tricyclohexylbenzene and 1,3,5-tricyclohexylbenzene, and combinations and mixtures thereof at any proportion. The generic term "polycycloyhexylbenzene" shall include any of the dicyclohexylbenzene isomers and tricyclohexylbenzene isomers described above, and combinations and mixtures of at least two thereof in any proportion.

Described herein is a process for producing phenol and cyclohexanone by cleavage of cyclohexyl-1-phenyl-1-hydroperoxide in the presence of a catalyst comprising sulfuric acid. In the process, the composition of the cleavage reaction mixture is adjusted, for example by recycling part of the cleavage effluent, and the cleavage conditions are controlled so as to maximize the yield of phenol and cyclohexanone.

The cleavage process as disclosed herein may form part of an integrated process for producing phenol from benzene in which the benzene is initially alkylated or hydroalkylated to produce cyclohexylbenzene and the cyclohexylbenzene is oxidized to produce cyclohexyl-1-phenyl-1-hydroperoxide. The ensuing description will therefore focus on this integrated process.

Production of Cyclohexylbenzene

The cyclohexylbenzene starting material for the present process can be produced by the alkylation of benzene with cyclohexene according to the following reaction:

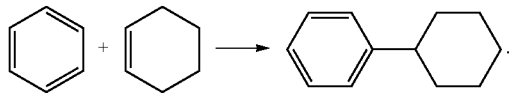

The cyclohexene can be supplied to the reaction zone as a separate feed from the benzene, but normally is produced in situ by the selective hydrogenation of benzene in the presence of a bifunctional catalyst. In the latter situation where cyclohexene is supplied in situ, the overall reaction is generally termed "hydroalkylation" and may be summarized as follows:

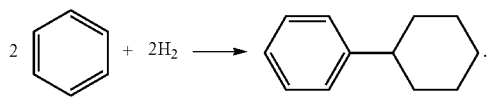

Any commercially available benzene feed can be used in the hydroalkylation step, but preferably the benzene has a purity level of at least 99 wt %. Similarly, although the source of hydrogen is not critical, it is desirable that the hydrogen is at least 99 wt % pure.

The total feed to the hydroalkylation step may contain less than 1000 ppm, such as less than 500 ppm, for example less than 100 ppm, water. In addition, the total feed may contain less than 100 ppm, such as less than 30 ppm, for example less than 3 ppm, sulfur and less than 10 ppm, such as less than 1 ppm, for example less than 0.1 ppm, nitrogen.

Hydrogen can be supplied to the hydroalkylation step over a wide range of values, but the hydrogen supply is desirably arranged such that the molar ratio of hydrogen to benzene in the hydroalkylation feed is from about 0.15:1 to about 15:1, such as from about 0.4:1 to about 4:1, for example from about 0.4:1 to about 0.9:1.

In addition to the benzene and hydrogen, a diluent, which is substantially inert under hydroalkylation conditions, may be supplied to the hydroalkylation reaction. The diluent can be a hydrocarbon, in which the desired cycloalkylaromatic product, in this case cyclohexylbenzene, is soluble, such as a straight chain paraffinic hydrocarbon, a branched chain paraffinic hydrocarbon, and/or a cyclic paraffinic hydrocarbon. Examples of suitable diluents are decane and cyclohexane. Cyclohexane is a particularly attractive diluent since it is an unwanted by-product of the hydroalkylation reaction.

Although the amount of diluent is not narrowly defined, advantageously the diluent is added in an amount such that the weight ratio of the diluent to the aromatic compound is at least 1:100; for example at least 1:10, but no more than 10:1, for example no more than 4:1.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are from about 100° C. to about 400° C., such as from about 125° C. to about 250° C., while suitable reaction pressures are from about 100 kPa to about 7,000 kPa, such as from about 500 kPa to about 5,000 kPa.

The catalyst employed in the hydroalkylation reaction is a bifunctional catalyst comprising a hydrogenating metal component and an alkylating solid acid component. Advantageously, the alkylating solid acid component comprises a molecular sieve of the MCM-22 family. The term "MCM-22 family material" (or "material of the MCM-22 family" or "molecular sieve of the MCM-22 family"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07, and 3.42±0.07 Angstrom. The X-ray diffraction data used to characterize the material are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), and mixtures thereof. UZM-8 (described in U.S. Pat. No. 6,756,030) may be used alone or in combination with any of the MCM-22 family molecular sieves. Preferably, the molecular sieve is selected from (a) MCM-49; (b) MCM-56; and (c) isotypes of MCM-49 and MCM-56, such as ITQ-2.

Any known hydrogenating metal can be employed in the hydroalkylation catalyst, although suitable metals include palladium, ruthenium, nickel, zinc, tin, and cobalt, with palladium being particularly advantageous. Desirably, the amount of hydrogenating metal present in the catalyst is from about 0.05 wt % to about 10 wt %, such as from about 0.1 wt % to about 5 wt %, of the catalyst. Where the MCM-22 family molecular sieve is an aluminosilicate, the amount of hydrogenating metal present may be such that the molar ratio of the aluminum in the molecular sieve to the hydrogenating metal is from about 1.5 to about 1500, for example from about 75 to about 750, such as from about 100 to about 300.

The hydrogenating metal may be directly supported on the MCM-22 family molecular sieve by, for example, impregnation or ion exchange. Preferably, at least 50 wt %, for example at least 75 wt %, and desirably substantially all of the hydrogenating metal is supported on an inorganic oxide separate from but composited with the molecular sieve. In particular, it is found that by supporting the hydrogenating metal on the inorganic oxide, the activity of the catalyst and its selectivity to cyclohexylbenzene and dicyclohexylbenzene are increased as compared with an equivalent catalyst in which the hydrogenating metal is supported on the molecular sieve.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13, and 14 of the Periodic Table of Elements, such as alumina, titania, and/or zirconia. As used herein, the numbering scheme for the Periodic Table Groups is as disclosed in Chemical and Engineering News, 63(5), 27 (1985).

The hydrogenating metal is deposited on the inorganic oxide by, e.g., impregnation, before the metal-containing inorganic oxide is composited with the molecular sieve. The catalyst composite may be produced by co-pelletization, in which a mixture of the molecular sieve and the metal-containing inorganic oxide are formed into pellets at high pressure (desirably about 350 kPa to about 350,000 kPa), or by co-extrusion, in which a slurry of the molecular sieve and the metal-containing inorganic oxide, optionally together with a separate binder, are forced through a die. If necessary, additional hydrogenating metal can subsequently be deposited on the resultant catalyst composite.

Although the hydroalkylation reaction using an MCM-22 family zeolite catalyst is highly selective towards cyclohexylbenzene, the effluent from the hydroalkylation reaction will inevitably contain some dicyclohexylbenzene by-product. Depending on the amount of this dicyclohexylbenzene, it may be desirable to either (a) transalkylate the dicyclohexylbenzene with additional benzene, or (b) dealkylate the dicyclohexylbenzene to maximize the production of the desired monoalkylated species.

Transalkylation with additional benzene may be conducted in a transalkylation reactor, separate from the hydroalkylation reactor, over a suitable transalkylation catalyst, such as a molecular sieve of the MCM-22 family, zeolite beta, MCM-68 (see U.S. Pat. No. 6,014,018), zeolite Y, and mordenite. The transalkylation reaction is desirably conducted under at least partial liquid phase conditions, which suitably include a temperature of about 100° C. to about 300° C., a pressure of about 800 kPa to about 3500 kPa, a weight hourly space velocity of about 1 $hr^{-1}$ to about 10 $hr^{-1}$ on total feed, and a benzene/dicyclohexylbenzene weight ratio of about 1:1 to about 5:1.

Dealkylation or cracking may also be effected in a reactor separate from the hydroalkylation reactor, such as a reactive distillation unit, at a temperature of about 150° C. to about 500° C. and a pressure of 15 psig to 500 psig (200 kPa to 3550 kPa) over an acid catalyst such as an aluminosilicate, an aluminophosphate, a silicoaluminphosphate, amorphous silica-alumina, an acidic clay, a mixed metal oxide, such as $WO_x/ZrO_2$, phosphoric acid, sulfated zirconia, and mixtures thereof. Desirably, the acid catalyst includes at least one aluminosilicate, aluminophosphate or silicoaluminphosphate of the FAU, AEL, AFI, and MWW family. Unlike transalkylation, dealkylation can be conducted in the absence of added benzene, although it may be desirable to add benzene to the dealkylation reaction to reduce coke formation. In this case, the weight ratio of benzene to poly-alkylated aromatic compounds in the feed to the dealkylation reaction is desirably from 0 to about 0.9, such as from about 0.01 to about 0.5. Similarly, although the dealkylation reaction can be conducted in the absence of added hydrogen, hydrogen is advantageously introduced into the dealkylation reactor to assist in coke reduction. Suitable hydrogen addition rates are such that the molar ratio of hydrogen to poly-alkylated aromatic compound in the total feed to the dealkylation reactor is from about 0.01 to about 10.

Another significant by-product of the hydroalkylation reaction is cyclohexane. Although a $C_6$-rich stream comprising cyclohexane and unreacted benzene can be readily removed from the hydroalkylation reaction effluent by distillation, owing to the similarity in the boiling points of benzene and cyclohexane, the $C_6$-rich stream is difficult to further separate by simple distillation. However, some or all of the $C_6$-rich stream can be recycled to the hydroalkylation reactor to provide not only part of the benzene feed but also part of the diluents mentioned above.

In some cases, it may be desirable to supply some of the $C_6$-rich stream to a dehydrogenation reaction zone, where the $C_6$-rich stream is contacted with a dehydrogenation catalyst under dehydrogenation conditions sufficient to convert at least part of the cyclohexane in the $C_6$-rich stream portion to benzene, which again can be recycled to the hydroalkylation reaction. The dehydrogenation catalyst desirably comprises (a) a support; (b) a hydrogenation-dehydrogenation component; and (c) an inorganic promoter. The support (a) may be selected from the group consisting of silica, a silicate, an aluminosilicate, zirconia, carbon nanotubes, and preferably comprises silica. Suitable hydrogenation-dehydrogenation components (b) comprise of at least one metal selected from Groups 6 to 10 of the Periodic Table of Elements, such as platinum, palladium, and compounds and mixtures thereof. Desirably, the hydrogenation-dehydrogenation component is present in an amount from about 0.1 wt % to about 10 wt % of the catalyst. A suitable inorganic promoter (c) comprises at least one metal or compound thereof selected from Group 1 of the Periodic Table of Elements, such as a potassium compound. The promoter may be present in an amount from about 0.1 wt % to about 5 wt % of the catalyst. Suitable dehydrogenation conditions include a temperature of about 250° C. to about 500° C., a pressure of about atmospheric to about 500 psig (100 kPa to 3550 kPa), a weight hourly space velocity of about 0.2 $hr^{-1}$ to 50 $hr^{-1}$, and a hydrogen to hydrocarbon feed molar ratio of about 0 to about 20.

Other disadvantageous impurities of the hydroalkylation reaction are bicyclohexyl (BCH) and the methylcyclopentylbenzene (MCPB) isomers which, because of the similarity in their boiling points, are difficult to separate from the desired cyclohexylbenzene by distillation. Moreover, although 1,2-methylcyclopentylbenzene (2-MCPB), and 1,3-methylcyclopentylbenzene (3-MCPB) are readily converted in the subsequent oxidation/cleavage steps to the phenol and methylcyclopentanones, which are valuable products, 1,1-methylcyclopentylbenzene (1-MCPB) is substantially inert to the oxidation step and so, if not removed, will build up in the $C_{12}$ stream. Similarly, bicyclohexyl (BCH) can lead to separation problems downstream. Thus, at least part of the hydroalkylation reaction product may be treated with a catalyst under conditions to remove at least 1,1-methylcyclopentylbenzene and/or bicyclohexyl from the product. The catalyst can be an acid catalyst, such as an aluminosilicate zeolite, and especially faujasite and the treatment is conducted at a temperature of about 100° C. to about 350° C., such as about 130° C. to about 250° C., for a time of about 0.1 to about 3 hours, such as about 0.1 to about 1 hour. The catalytic treatment is believed to isomerize the 1,1-methylcyclopentylbenzene to the more readily oxidizable 1,2-methylcyclopentylbenzene (2-MCPB), and 1,3-methylcyclopentylbenzene (3-MCPB). The bicyclohexyl is believed to react with benzene present in the hydroalkylation reaction product to produce cyclohexane and more of the desired cyclohexylbenzene according to the following reaction:

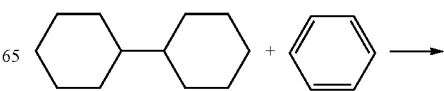

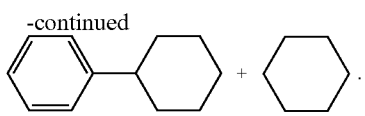

The catalytic treatment can be conducted on the direct product of the hydroalkylation reaction or after distillation of the hydroalkylation reaction product to separate the $C_6$ and/or the heavies fraction.

The cyclohexylbenzene product from the hydroalkylation reaction and any downstream reaction to remove the impurities discussed herein is separated from the reaction effluent(s) and is fed to the oxidation reaction described in more detail below.

Cyclohexylbenzene Oxidation

In order to convert the cyclohexylbenzene into phenol and cyclohexanone, the cyclohexylbenzene is initially oxidized to the corresponding hydroperoxide, particularly cyclohexyl-1-phenyl-1-hydroperoxide. This is accomplished by contacting the cyclohexylbenzene with an oxygen-containing gas, such as air and various derivatives of air. For example, it is possible to use air that has been compressed and filtered to removed particulates, air that has been compressed and cooled to condense and remove water, or air that has been enriched in oxygen above the natural approximately 21 mol % in air through membrane enrichment of air, cryogenic separation of air or other conventional means.

The oxidation step can be conducted, autogenously or more preferably, in the presence of a catalyst. Although any catalyst can be employed, a preferred oxidation catalyst includes an N-hydroxy substituted cyclic imide described in U.S. Pat. No. 6,720,462, which is incorporated herein by reference in its entirety for this purpose. For example, N-hydroxyphthalimide (NHPI), 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt or N-hydroxy-o-benzenedisulphonimide may be used. The catalyst can be N-hydroxyphthalimide. Another suitable catalyst is N,N',N"-trihydroxyisocyanuric acid. Each of the above cyclic imide catalysts contain the heteroatom nitrogen.

These oxidation catalysts can be used either alone or in conjunction with a free radical initiator, and further can be used as liquid-phase, homogeneous catalysts or can be supported on a solid carrier to provide a heterogeneous catalyst. Desirably, the N-hydroxy substituted cyclic imide or the N,N',N"-trihydroxyisocyanuric acid is employed in an amount from 0.0001 wt % to 15 wt %, such as from 0.001 wt % to 5 wt %, of the cyclohexylbenzene.

Suitable conditions for the oxidation step include a temperature from about 70° C. to about 200° C., such as about 90° C. to about 130° C., and a pressure of about 50 kPa to 10,000 kPa. A basic buffering agent may be added to react with acidic by-products that may form during the oxidation. In addition, an aqueous phase may be introduced. The reaction can take place in a batch or continuous flow fashion.

The reactor used for the oxidation reaction may be any type of reactor that allows for introduction of oxygen to cyclohexylbenzene, and may further efficaceously provide contacting of oxygen and cyclohexylbenzene to effect the oxidation reaction. For example, the oxidation reactor may comprise a simple, largely open vessel with a distributor inlet for the oxygen-containing stream. The oxidation reactor may have means to withdraw and pump a portion of its contents through a suitable cooling device and return the cooled portion to the reactor, thereby managing the exothermicity of the oxidation reaction. Alternatively, cooling coils providing indirect cooling, say by cooling water, may be operated within the oxidation reactor to remove the generated heat. Alternatively, the oxidation reactor may comprise a plurality of reactors in series, each conducting a portion of the oxidation reaction, optionally operating at different conditions selected to enhance the oxidation reaction at the pertinent conversion range of cyclohexylbenzene or oxygen, or both, in each. The oxidation reactor may be operated in a batch, semi-batch, or continuous flow manner.

Desirably, the product of the cyclohexylbenzene oxidation reaction contains at least 5 wt %, such as at least 10 wt %, for example at least 15 wt %, or at least 20 wt % cyclohexyl-1-phenyl-1-hydroperoxide based upon the total weight of the oxidation reaction effluent. Desirably, the oxidation reaction effluent contains no greater than 80 wt %, or no greater than 60 wt %, or no greater than 40 wt %, or no greater than 30 wt %, or no greater than 25 wt % of cyclohexyl-1-phenyl-1-hydroperoxide based upon the total weight of the oxidation reaction effluent. The oxidation reaction effluent may contain up to 5 wt %, desirably no more than 3 wt %, of peroxides other than cyclohexyl-1-phenyl-1-hydroperoxide.

The oxidation reaction effluent may also comprise unreacted cyclohexylbenzene. For example, the oxidation reaction effluent may include unreacted cyclohexylbenzene in an amount of at least 50 wt %, or at least 60 wt %, or at least 65 wt %, or at least 70 wt %, or at least 80 wt %, or at least 90 wt %, based upon total weight of the oxidation reaction effluent.

Treatment of the Oxidation Reaction Effluent

In addition to cyclohexyl-1-phenyl-1-hydroperoxide and unreacted cyclohexylbenzene, the oxidation reaction effluent may also contain some of the cyclic imide used as a catalyst in the oxidation reaction. The oxidation reaction effluent (oxidation product) may be used as the cleavage feed and contains the cyclic imide catalyst. No significant adverse effect has been detected from having the cyclic imide present in the cleavage reaction mixture. However, since cyclic imides are expensive and may act as poisons to some downstream reactions, it may be desirable to remove and/or recover at least part of the cyclic imide from the oxidation reaction effluent for recycle back to the oxidation step. Removal of the cyclic imide can comprise contacting the oxidation reaction effluent with an aqueous solution of a base, particularly a weak base having a pKb value greater than or equal to the pKa of the cyclic imide of the first catalyst, whereby the imide is extracted into the aqueous phase, leaving an organic phase which comprises said oxidized hydrocarbon product and a reduced level of cyclic imide. Alternatively, treatment of the oxidation effluent to remove at least part of the cyclic imide comprises contacting the effluent with an effective solid sorbent, such as a metal oxide or a metal carbonate and/or hydrogen carbonate.

Prior to feeding to the cleavage step, the oxidation reaction effluent may be treated to increase the concentration of the cyclohexyl-1-phenyl-1-hydroperoxide. Suitable concentration steps include fractional distillation to remove at least part of the higher boiling cyclohexylbenzene and fractional crystallization to separate solid cyclohexyl-1-phenyl-1-hydroperoxide from the oxidation reaction effluent. The concentration step(s) are used to produce a cleavage feed containing greater than 40 wt % and no greater than 95 wt %, for example from 60 wt % to 85 wt %, of cyclohexyl-1-phenyl-1-hydroperoxide, and at least 5 wt % and less than 60 wt %, for example from 15 wt % to 40 wt %, of cyclohexylbenzene.

Hydroperoxide Cleavage

The final reactive step in the conversion of the cyclohexylbenzene into phenol and cyclohexanone involves the acid-catalyzed cleavage of the cyclohexyl-1-phenyl-1-hydroperoxide produced in the oxidation step, potentially after such treatment or concentration discussed earlier herein. The catalyst employed in the cleavage reaction comprises sulfuric acid. Other hydroperoxides that may be present in the cleavage feed may also undergo acid-catalyzed cleavage, along with the desired cyclohexyl-1-phenyl-1-hydroperoxide.

In the present process, the composition of cleavage feed is initially adjusted by mixing the cleavage feed with at least phenol, cyclohexanone, water, and sulfuric acid, to produce a cleavage reaction mixture containing from 15 wt % to 50 wt % phenol, from 15 wt % to 50 wt % cyclohexanone, from 1 wt % to 10 wt % cyclohexyl-1-phenyl-1-hydroperoxide, from 5 wt % to 60 wt % cyclohexylbenzene, from 0.1 wt % to 4 wt % water, and from 10 wppm to 1000 wppm sulfuric acid. The cleavage reaction mixture may contain from 25 wt % to 45 wt % phenol, from 25 wt % to 45 wt % cyclohexanone, from 1 wt % to 6 wt % cyclohexyl-1-phenyl-1-hydroperoxide, from 15 wt % to 40 wt % cyclohexylbenzene, from 0.5 wt % to 3.0 wt % water, and from 20 wppm and to 500 wppm sulfuric acid. Alternatively, the cleavage reaction mixture contains from 30 wt % to 40 wt % phenol, from 30 wt % to 40 wt % cyclohexanone, from 1 wt % to 5 wt % cyclohexyl-1-phenyl-1-hydroperoxide, from 15 wt % to 40 wt % cyclohexylbenzene, from 0.5 wt % to 2.0 wt % water, and from 40 wppm and to 200 wppm sulfuric acid. Still alternatively, the cleavage reaction mixture contains at least 1 wt % more phenol than the wt % of cyclohexanone, for example so that the weight ratio of phenol to cyclohexanone in said cleavage reaction mixture is in excess of 1:1, desirably from 1.05:1 to 10:1.

Adjustment of the composition of the cleavage feed may be achieved by mixing the cleavage feed with a recycle stream comprising part of the cleavage effluent since the latter contains phenol, cyclohexanone, cyclohexyl-1-phenyl-1-hydroperoxide, cyclohexylbenzene, water, and sulfuric acid. Mixing with the cleavage recycle stream may be sufficient to achieve the desired reaction mixture composition. Where necessary, however, the desired water content in the cleavage reaction mixture can be obtained by one or more of adding water to the cleavage feed, mixing the cleavage feed with the cleavage recycle stream and with water, adding water to the cleavage recycle stream, and adding water to the cleavage effluent. Similarly, the desired sulfuric acid content in the cleavage reaction mixture can be obtained by one or more of adding sulfuric acid to the cleavage feed, mixing the cleavage feed with the cleavage recycle stream and with sulfuric acid, adding sulfuric acid to the cleavage recycle stream, and adding sulfuric acid to the cleavage effluent. In addition, the desired phenol content in the cleavage reaction mixture can be obtained by one or more of adding phenol to the cleavage feed, mixing the cleavage feed with the cleavage recycle stream and with phenol, adding phenol to the cleavage recycle stream, and adding phenol to the cleavage effluent.

The cleavage reaction is conducted under conditions including a temperature from 30° C. and to 70° C., such as from 40° C. to 60° C. and a pressure of at least 1 atmosphere, such as from 100 KPaa to 2000 kPaa). The cleavage conditions are desirably selected so that the cleavage reaction mixture is completely or predominantly in the liquid phase during the cleavage reaction and so that the reaction occurs at a cyclohexyl-1-phenyl-1-hydroperoxide (CHBHP) first order rate constant from 0.1 $min^{-1}$ to 20 $min^{-1}$. Alternatively, the CHBHP first order rate constant may be from 0.5 $min^{-1}$ to 15 $min^{-1}$, or from 1 $min^{-1}$ to 12 $min^{-1}$. The cleavage reaction may be conducted for a time sufficient to convert at least 50%, desirably at least 75%, of the cyclohexyl-1-phenyl-1-hydroperoxide in the cleavage reaction mixture and produce a cleavage effluent containing phenol and cyclohexanone.

The reactor used to effect the cleavage reaction may be any type of reactor known to those skilled in the art. For example, the cleavage reactor may be a simple, largely open vessel operating in a near-continuous stirred tank reactor mode, or a simple, open length of pipe operating in a near-plug flow reactor mode. Alternatively, the cleavage reactor comprises a plurality of reactors in series, each performing a portion of the conversion reaction, optionally operating in different modes and at different conditions selected to enhance the cleavage reaction at the pertinent conversion range. The cleavage process may be run on a continuous basis. It is also possible to run the process in a batch reactor.

The cleavage reactor can be operable to transport a portion of the contents through a cooling device and return the cooled portion to the cleavage reactor, thereby managing the exothermicity of the cleavage reaction. Cooling coils operating within the cleavage reactor(s) can be used to remove at a least part of the heat generated. Alternatively, the reactor may be operated adiabatically. Alternatively, the cleavage effluent taken from the cleavage reactor can be cooled and at least a portion of the cooled cleavage effluent is divided into a cooled cleavage recycle to be mixed with the cleavage feed.

The major products of the cleavage reaction are phenol and cyclohexanone, which are present in substantially equimolar amounts and, by virtue of the present process, are obtained in high yield. As discussed above, primary by-products of the cleavage of cyclohexyl-1-phenyl-1-hydroperoxide may include the β-scission products such as hexanophenone and 6-hydroxylhexanophenone (6-HHP). Examples of secondary by-products include those derived from cyclohexanone, such as 2-(1-cyclohexenyl)cylohexanone and 2-(cyclohexylidene)cyclohexanone (cyclohexanone aldol condensation products), 2-hydroxycyclohexanone and cyclohexenone (cyclohexanone oxidation products). In the present process the formation of these by-products is reduced so that, for example, the amount of 6-hydroxylhexanophenone (6-HHP) in the cleavage effluent may be no greater than 5 wt %, or no greater than 2 wt %.

On leaving the cleavage reactor, the cleavage effluent may be cooled and thereafter separated into a product stream, from which the phenol and cyclohexanone products can be recovered, and a cleavage recycle stream, which can be mixed with the cleavage feed. Separation of the cleavage recycle stream can be effected without prior modification of the composition of cleavage effluent so that the recycle stream is composed of an aliquot of the cleavage effluent. The cleavage recycle may have substantially the same composition as the cleavage effluent, say within 2 wt % or even within 1 wt % of any given species content in the cleavage effluent, for example, as may be indirectly affected by reactions occurring on the cleavage recycle in conveyance to the mixing with the cleavage feed. Thus, the cleavage feed may further be mixed with cyclohexylbenzene and/or cyclohexyl-1-phenyl-1-hydroperoxide, in addition to at least phenol, cyclohexanone, water and sulfuric acid, for example, as may all be present in the portion of the cleavage effluent allocated as cleavage recycle.

Alternatively, the cleavage effluent or a portion thereof can be treated, for example, by fractionation, to separate the by-products and/or other components of the cleavage effluent. Those components may include phenol, cyclohexanone and water, which may be used to provide at least some of the phenol, cyclohexanone or water for mixing with the cleavage feed to attain the desired cleavage reaction mixture composition.

Some of the residual sulfuric acid in the cleavage reaction effluent may be initially neutralized by treating the cleavage effluent with one or more basic compounds. Suitable basic compounds include amines or diamines, for example, 2-methylpentane-1,5 diamine.

The present disclosure will now be more particularly described with reference to the following non-limiting examples and FIG. 1 of the accompanying drawing.

In the examples, all parts and percentages and by weight unless otherwise indicated.

Example 1

A series of cleavage reaction mixtures were provided, each comprising cyclohexyl-1-phenyl-1-hydroperoxide (CHBHP) and cyclohexylbenzene (CHB), together with cyclohexanone (CHone), phenol, acetone and/or water in varying amounts. The cyclohexyl-1-phenyl-1-hydroperoxide used in each mixture was prepared according to Example 2, below and the composition of each mixture is summarized in Table 1. Experiments were then ran to investigate the composition of the cleavage reaction mixture on the first order rate constant for the cleavage of cyclohexyl-1-phenyl-1-hydroperoxide (CHBHP) in the presence of a sulfuric acid catalyst. In each experiment, the cleavage reaction was conducted as follows.

An amount of 75 g of each mixture was separately charged to a 100-mL jacketed glass reactor fitted with a circulating temperature bath set to 50° C. The reactor content was allowed to equilibrate and then an amount of 5% $H_2SO_4$ solution in 1,2-dimethoxyethane was injected into the reactor to give 50 wppm sulfuric acid in the cleavage reaction mixture with respect to the total contents in the reactor. The acid was injected in a single dose in all experiments with the exception of 1(d), highlighted with a single asterisk in Table 1, in which the acid was injected in two doses, the first providing 25 wppm of acid, and the second following one minute later providing a total of 50 wppm acid.

After a brief reaction exotherm upon introduction of the sulfuric acid, as indicated by a temperature rise inside the reactor, one gram aliquots were taken at certain time intervals and neutralized with DYTEK A® in slight excess to the amount of sulfuric acid. The aliquot samples generated were analyzed by GC. The results are summarized in FIG. 1 and Table 1.

In FIG. 1, the first order rate constant is plotted against the sum of all components in the cleavage reaction mixture other than CHB. As will be seen from FIG. 1, the rate constant for CHBHP cleavage increases as the CHB content is decreased.

The effect of adding phenol, cyclohexanone or acetone to the reaction mixture can be seen from Table 1. In each case, addition of phenol, cyclohexanone or acetone leads to an increase in the rate constant for CHBHP cleavage.

As seen in Table 1, addition of water to the reaction mixture causes slowing down of the CHBHP cleavage reaction. The addition of water directly to the reaction mixture or in conjunction with one of the other components (for example, sulfuric acid) can be used to dampen the CHBHP reaction rate, if desired.

TABLE 1

| Mixture | CHBHP (wt %) | CHB (wt %) | Phenol (wt %) | CHone (wt %) | Water (wppm) | CHB-HP Rate (k, min$^{-1}$) |
|---------|--------------|------------|---------------|--------------|--------------|------------------------------|
| 1(a)    | 3.0          | 60.0       | 18.5          | 18.5         | 0            | 4.1                          |
| 1(b)    | 3.0          | 60         | 18.5          | 18.4         | 1000         | 3.88                         |
| 1(c)    | 3.0          | 60         | 18.0          | 18.0         | 10000        | 2.1                          |
| 1(d)*   | 3.0          | 60         | 18.5          | 18.5         | 0            | 1.6                          |
| 2(a)    | 3.0          | 12.5       | 42.3          | 42.2         | 0            | 11.1                         |
| 2(b)    | 3.0          | 12.5       | 42.3          | 42.2         | 500          | 9.36                         |
| 2(c)    | 3.0          | 12.5       | 42.3          | 42.2**       | 0            | 9.53                         |
| 3(a)    | 3.0          | 97         | 0             | 0            | 0            | 0.016                        |
| 3(b)    | 3.0          | 97         | 0             | 0            | 500          | 0.03                         |
| 4       | 6.0          | 75         | 9.5           | 9.5          | 0            | 1.8                          |

All experiments run at 50 wppm sulfuric acid provided in a single dose, except *, where sulfuric acid added in two doses providing 25 wppm each.
**Acetone is used in place of CHone.

Although not shown in FIG. 1 or Table 1, the selectivity of CHBHP conversion towards the primary products phenol and cyclohexanone, particularly the selectivity to cyclohexanone, is improved by decreasing CHB content and increasing phenol and cyclohexanone content in the cleavage reaction mixture.

Example 2

An amount of 631 g of cyclohexylbenzene (CHB, TCI America, Inc.) was added to a 1-liter four-necked glass flask, to which 0.6702 g of NHPI (TCI America, Inc.) was added. The flask was then fitted with a reflux condenser, a mechanical stirrer, a gas sparger, and a thermometer. An air flow of 250 cc/min was bubbled through the liquid via the gas sparger; and the content was heated at 110° C. with stirring (560 rpm) for 6 hr. The flask was allowed to cool down to room temperature and the oxidation product recovered. GC analysis indicated the product to contain 17.9 wt % CHBHP.

The CHB oxidation product was seeded with 0.5 g of CHBHP crystals and stored in a refrigerator at −5° C. Solid CHBHP started to form in a day; and the sample was stored in the refrigerator for a week to maximize the amount of CHBHP precipitated. The sample was then taken out, the solid filtered, washed with cold pentane, and dried under vacuum. The resultant solid CHBHP product contains 95% CHBHP (the rest is residual CHB, with trace amounts of phenol and hexanophenone).

The solid CHBHP product was combined with CHB, phenol, cyclohexanone and dodecane (as internal standard) to form a mixture composed of 5 wt % CHBHP, 15 wt % CHB, 35 wt % phenol, 35 wt % cyclohexanone, and 10 wt % dodecane. An amount of 20 g of the mixture was charged to a 50-mL jacketed glass reactor with a circulating temperature bath. The bath was set to 50° C. and the reactor content was allowed to equilibrate. An amount of 11.5 microliters of 5% sulfuric acid solution in 1,2-dimethoxyethane was then injected to the reactor (to give 25 ppm $H_2SO_4$ in the reactor). After a brief reaction exotherm, as indicated by the temperature rise inside the reactor, one gram aliquot was taken at certain time intervals and neutralized with dihexylamine. The samples generated were analyzed by GC.

The experiment was then repeated by adding desired amounts of water to the cleavage reaction mixture. The data are summarized in Table 2 and demonstrate that the addition of water significantly reduces formation of 6-hydroxy-hexanophenone (6-HHP) and improves selectivity to phenol and cyclohexanone.

TABLE 2

| $H_2SO_4$ (ppm) | $H_2O$ added (wt %) | Rate (k, min$^{-1}$) | Mol. Selectivity (%) | | | |
|---|---|---|---|---|---|---|
| | | | CHone | PhOH | 2-OHCHone | 6-HHP |
| 25 | 0 | too fast to measure | 83.7 | 88.7 | 0 | 14.9 |
| 25 | 1 | 0.75 | 88.3 | 98.5 | 0.6 | 6.9 |
| 25 | 1.5 | 0.11 | 93.4 | 98.2 | 0.7 | 4.3 |

In Table 2, CHone=cyclohexanone; PhOH=phenol; and 2-OHCHone=2-hydroxycyclohexanone. Selectivities are compared at 95-98% conversion levels.

Example 3

The oxidation product from Example 2 was diluted with phenol and cyclohexanone to give a cleavage reaction mixture containing CHBHP/CHB/phenol/cyclohexanone in the ratio of 4/15/35.5/35.5 wt %; the balance is dodecane (10 wt %, internal standard). An amount of 20 g of the mixture was charged to a 50-mL jacketed glass reactor with a circulating temperature bath. The bath was set to 50° C. and the reactor content was allowed to equilibrate. An amount of 11.5 microliters of 5% sulfuric acid solution in 1,2-dimethoxyethane was then injected to the reactor (to give 25 ppm $H_2SO_4$ in the reactor). After a brief reaction exotherm, as indicated by the temperature rise inside the reactor, one gram aliquot was taken at certain time interval and neutralized with dihexylamine. The samples generated were analyzed by GC.

The experiment was then repeated after adding water to the cleavage reaction mixture such that the water content was 0.5 wt % of the mixture. The data are summarized in Table 3 and again demonstrate that the addition of water significantly reduces formation of 6-hydroxyhexanophenone (6-HHP) and improves selectivity to phenol and cyclohexanone.

TABLE 3

| $H_2SO_4$ (ppm) | $H_2O$ added (wt %) | Mol. Selectivity (%) | | | |
|---|---|---|---|---|---|
| | | CHone | PhOH | 2-OHCHone | 6-HHP |
| 25 | 0 | 87 | 89 | 0 | 12.4 |
| 25 | 0.5 | 90 | 99 | 0 | 6.4 |

In Tables 3 and 4, CHone=cyclohexanone; PhOH=phenol; and 2-OHCHone=2-hydroxycyclohexanone. Selectivities are compared at 95-98% conversion levels.

Example 4

The solid CHBHP product from Example 2 was combined with CHB, phenol, cyclohexanone, and dodecane (as internal standard) to form a cleavage reaction mixture composed of 5 wt % CHBHP, 65 wt % CHB, 10 wt % dodecane and the concentrations of phenol and cyclohexanone shown in Table 4. An amount of 20 g of the mixture was charged to a 50-mL jacketed glass reactor with a circulating temperature bath. The bath was set to 50° C. and the reactor content was allowed to equilibrate. An amount of 11.5 microliters of 5% sulfuric acid solution in 1,2-dimethoxyethane was then injected to the reactor (to give 25 ppm $H_2SO_4$ in the reactor). After a brief reaction exotherm, as indicated by the temperature rise inside the reactor, one gram aliquot was taken at certain time interval and neutralized with dihexylamine. The samples generated were analyzed by GC and the results are shown in Table 4, where selectivities are again compared at 95-98% conversion levels.

TABLE 4

| | PhOH (wt %) | CHone (wt %) | CHone sel. (mol %) | PhOH sel. (mol %) |
|---|---|---|---|---|
| Run 1 | 10 | 10 | 91.4 | 95.7 |
| Run 2 | 15 | 5 | 98.6 | 100 |
| Run 3 | 13 | 7 | 97.7 | 95.7 |

The data in Table 4 clearly show that yield to phenol and cyclohexanone is improved by controlling the ratio of phenol to cyclohexanone in the cleavage reaction mixture.

Various embodiments of the present disclosure will now be more particularly described with reference to FIGS. 2 to 4 the accompanying drawings.

Figure 2:
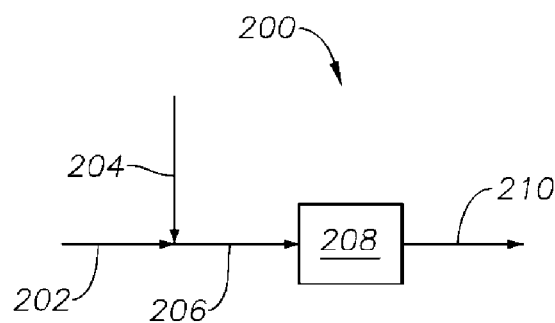
FIGS. 2 to 4 are flow diagrams of three exemplary processes for producing phenol and cyclohexanone.

FIG. 2 is a schematic view of an exemplary process 200 for producing phenol and cyclohexanone, in which a cleavage feed, containing greater than 40 wt % and no greater than 95 wt % cyclohexyl-1-phenyl-1-hydroperoxide and at least 5 wt % and less than 60 wt % cyclohexylbenzene, is provided in line 202. The cleavage feed in line 202 is mixed with an appropriate amount of phenol, cyclohexanone, water and sulfuric acid provided in line 204, selected to provide a cleavage reaction mixture in line 206 containing from 15 wt % to 50 wt % phenol, from 15 wt % to 50 wt % cyclohexanone, from 1 wt % to 10 wt % cyclohexyl-1-phenyl-1-hydroperoxide, from 5 wt % to 60 wt % cyclohexylbenzene, from 0.1 wt % to 4 wt % water, and from 10 wppm to 1000 wppm sulfuric acid.

The sources of phenol, cyclohexanone, water and sulfuric acid provided in line 204 may be any that are convenient. This includes sources attached to or associated with production process 200, such as dividing, separation or other downstream processing of the cleavage effluent in line 210, or sources auxiliary to process 200, for example a water production unit that is part of a greater facility employing process 200, or sources external to production process 200, such as material made by or purchased from a third party. Also, the phenol, cyclohexanone, water, and sulfuric acid provided in line 204 may alternatively be provided discretely, that is, in separate lines at various locations in various orders, in the mixing with the cleavage feed to provide the cleavage reaction mixture in line 206 of the requisite composition.

The cleavage feed mixture in line 206 is provided to cleavage reactor 208, where reacting takes place at a temperature from about 30 C to about 70° C., and a pressure of at least 1 atmosphere for a time sufficient to convert at least 50% of said cyclohexyl-1-phenyl-1-hydroperoxide in said cleavage reaction mixture, and produce a cleavage effluent containing phenol and cyclohexanone in line 210.

Figure 3:
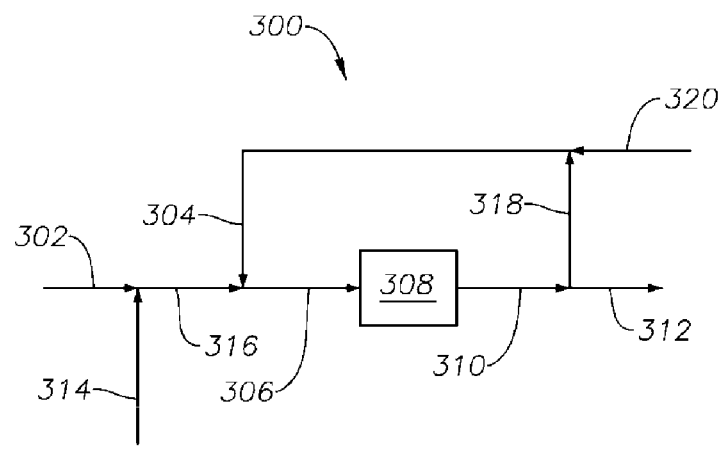

FIG. 3 is a schematic view of another exemplary process 300 for producing phenol and cyclohexanone, in which a cleavage feed is provided in line 302 and is mixed with make-up water in line 314 to provide a wet cleavage feed in line 316. The wet cleavage feed in line 316 is then mixed with an acid-supplemented cleavage recycle in line 304 to provide a cleavage reaction mixture in line 306. The acid-supplemented cleavage recycle in line 304 is derived from the cleavage effluent in line 310, and thus further contains phenol, cyclohexanone, water and cyclohexylbenzene, in addition to sulfuric acid as present in the cleavage effluent in line 310 and as supplemented. Rates and compositions of the cleavage feed in line 302, the make-up water in line 314, and the acid-supplemented cleavage recycle in line 304 (and by extension the rates and compositions of make-up sulfuric acid in line 320 and the cleavage recycle in line 318) are correlated to provide the cleavage reaction mixture in line 306 of the requisite composition.

The cleavage reaction mixture in line 306 is provided to cleavage reactor 308, where reacting takes place at the requisite conditions to produce a cleavage effluent in line 310 containing phenol and cyclohexanone, and as noted above, further containing cyclohexylbenzene, water, and sulfuric acid. Depending on the extent of conversion of the cyclohexyl-1-phenyl-1-hydroperoxide in the cleavage reaction mixture in line 306, the cleavage effluent in line 310 may also contain unreacted cyclohexyl-1-phenyl-1-hydroperoxide.

The cleavage effluent in line 310 is divided, in this case with no pretreatment or separation, into a cleavage product in line 312 and a cleavage recycle in line 318. Thus, the cleavage effluent in line 310, the cleavage product in line 312, and the cleavage recycle in line 318 will in this exemplary process have identical composition, though their rates may be significantly different according to the appropriate correlation noted above. The cleavage recycle in line 318 is mixed with make-up sulfuric acid in line 320 to provide the acid-supplemented cleavage recycle in line 304. The cleavage product in line 312 may undergo further processing, for example, to neutralize the sulfuric acid contained therein, or to recover, separate and purify the phenol and cyclohexanone components therein and render them of salable quality, or recover and recycle the cyclohexylbenzene therein to an oxidation reaction that provides cyclohexyl-1-phenyl-1-hydroperoxide for use in the process 300, and the like.

Figure 4:
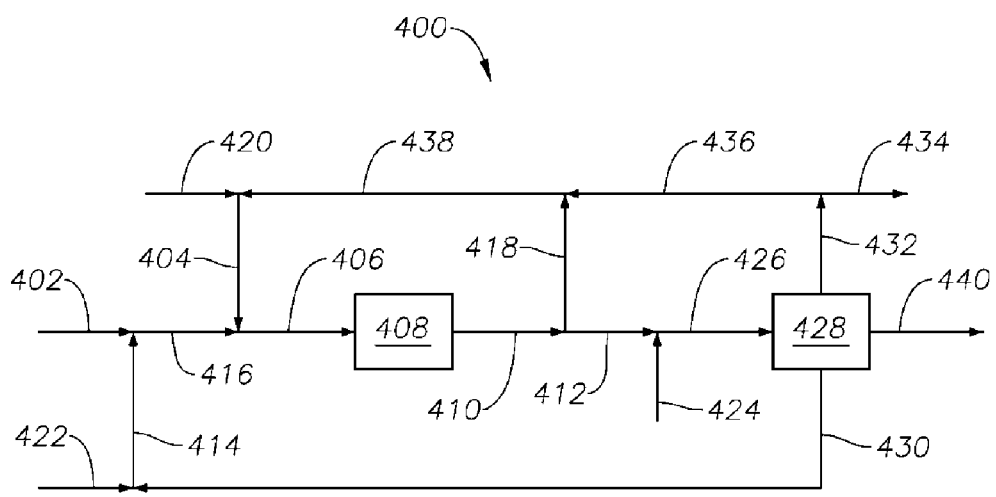

FIG. 4 is a schematic view of yet another example of a process 400 for producing phenol and cyclohexanone. In this process 400, a cleavage feed is provided in line 402 that is mixed with combined water in line 414 to provide a wet cleavage feed in line 416. The wet cleavage feed in line 416 is then mixed with a phenol-and-acid-supplemented cleavage recycle in line 404 to provide a cleavage reaction mixture in line 406.

The phenol-and-acid-supplemented cleavage recycle in line 404 is derived from the cleavage effluent in line 410, and thus further contains cyclohexanone, water and cyclohexylbenzene, in addition to phenol and sulfuric acid as present in the cleavage effluent in line 410 and as supplemented. Rates and compositions of the cleavage feed in line 402, the combined water in line 414 (and by extension the make-up water in line 422 and the recycle water in line 430), and the phenol-and-acid-supplemented cleavage recycle in line 404 (and by extension the rates and compositions of the recycle phenol in line 436, make-up sulfuric acid in line 420 and the cleavage recycle in line 418) are correlated to provide the cleavage reaction mixture in line 406 of the requisite composition.

The cleavage reaction mixture in line 406 is provided to cleavage reactor 408, where reacting takes place at the requisite conditions to produce a cleavage effluent in line 410 containing phenol and cyclohexanone, and as noted above, further containing cyclohexylbenzene, water, and sulfuric acid. Depending on the extent of conversion of the cyclohexyl-1-phenyl-1-hydroperoxide in the cleavage reaction mixture in line 406, the cleavage effluent in line 410 may also contain unreacted cyclohexyl-1-phenyl-1-hydroperoxide.

The cleavage effluent in line 410 is divided, in this case with no pretreatment or separation, into a cleavage product in line 412 and a cleavage recycle in line 418. Thus, the cleavage effluent in line 410, the cleavage product in line 412 and the cleavage recycle in line 418 will in this exemplary process have identical composition, though their rates may be significantly different according to the appropriate correlation noted above.

The cleavage recycle in line 418 is mixed with a phenol recycle in line 436 to provide a phenol-supplemented cleavage recycle in line 438. The phenol-supplemented cleavage recycle in line 438 is then mixed with make-up sulfuric acid in line 420 to provide the aforementioned phenol-and-acid-supplemented cleavage recycle in line 404.

The cleavage product in line 412 is mixed with an amine in line 424 of a type, for example, DYTEK A®, and a rate calculated to complex with and neutralize the sulfuric acid contained in the cleavage product in line 412, arrest the catalytic activity of the sulfuric acid, and provide a largely unreactive, neutralized cleavage product in line 426.

The neutralized cleavage product in line 426 is provided to a separation and recovery section 428. As one possible operation of separation and recovery section 428, a stream containing largely water is generated as recycle water in line 430. The recycle water in line 430 is mixed with the make-up water in line 422 to provide the combined water in line 414, discussed above. Another possible operation of separation and recovery section 428 is the generation of a stream containing largely phenol in line 432. The largely phenol stream in line 432 is divided into a phenol draw in line 434, which may undergo further processing to make high quality, sales grade phenol, and the phenol recycle in line 436, discussed above. Finally, a remainder stream may be withdrawn from separations and recovery sections 428 in line 440. The remainder stream in line 440 represents the other components present in the neutralized cleavage product in line 426, such as cyclohexanone, unreacted cyclohexylbenzene and cleavage reaction byproducts, and may further include minor amounts of phenol and water, and may be directed to further processing, for example, to make high quality, sales grade cyclohexanone or recycle cyclohexylbenzene, as discussed above. Alternatively, those other components represented in the remainder stream in line 440 may be generated in higher concentrations and withdrawn from separation and recovery section 428 in multiple discrete streams.

While the present invention has been described and illustrated by reference to particular embodiments, those of ordinary skill in the art will appreciate that the present disclosure lends itself to variations not necessarily illustrated herein. For this reason, then, reference should be made solely to the appended claims for purposes of determining the true scope of the present invention. Contents of all references cited herein are incorporated by reference in their entirety.

The invention claimed is:

1. A process for producing phenol and cyclohexanone, the process comprising:
   (a) providing a cleavage feed containing greater than 40 wt % and no greater than 95 wt % cyclohexyl-1-phenyl-1-hydroperoxide, and at least 5 wt % and less than 60 wt % cyclohexylbenzene;
   (b) mixing said cleavage feed with at least phenol, cyclohexanone, water, and sulfuric acid, to produce a cleavage reaction mixture containing from 15 wt % to 50 wt % phenol, from 15 wt % to 50 wt % cyclohexanone, from 1 wt % to 10 wt % cyclohexyl-1-phenyl-1-hydroperoxide, from 5 wt % to 60 wt % cyclohexylbenzene, from 0.1 wt % to 4 wt % water, and from 10 wppm to 1000 wppm sulfuric acid; and
   (c) reacting said cleavage reaction mixture at a temperature from 30° C. and to 70° C. for a time sufficient to convert at least 50% of said cyclohexyl-1-phenyl-1-hydroperoxide in said cleavage reaction mixture and produce a cleavage effluent containing phenol and cyclohexanone.

2. The process of claim 1, wherein said cleavage feed contains from 60 wt % to wt % cyclohexyl-1-phenyl-1-hydroperoxide and from 15 wt % to 40 wt % cyclohexylbenzene.

3. The process of claim 1, wherein said cleavage reaction mixture contains from 25 wt % to 45 wt % phenol, from 25 wt % to 45 wt % cyclohexanone, from 1 wt % to 6 wt % cyclohexyl-1-phenyl-1-hydroperoxide, from 15 wt % to 40 wt % cyclohexylbenzene, from 0.5 wt % to 3.0 wt % water, and from 20 wppm to 500 wppm sulfuric acid.

4. The process of claim 1, wherein said process is continuous, and said reacting (c) is conducted at a temperature from 40° C. to 60° C.

5. The process of claim 1, wherein said reacting (c) converts at least 75% of said cyclohexyl-1-phenyl-1-hydroperoxide in said cleavage reaction mixture.

6. The process of claim 1, wherein said reacting (c) occurs at a cyclohexyl-1-phenyl-1-hydroperoxide rate constant from 0.1 $min^{-1}$ to 20 $min^{-1}$.

7. The process of claim 1, wherein the cleavage reaction mixture contains at least 1 wt % more phenol than the weight percentage of cyclohexanone.

8. The process of claim 1 and further including (d) dividing said cleavage effluent into at least a cleavage product and a cleavage recycle, wherein said cleavage recycle provides at least a portion of said phenol, water, and sulfuric acid mixed with said cleavage feed in step (b).

9. The process of claim 8, wherein at least a portion of said water mixed with said cleavage feed in step (b) is provided by one or more of adding water to said cleavage feed, mixing said cleavage feed with said cleavage recycle and with water, adding water to said cleavage recycle, and adding water to said cleavage effluent.

10. The process of claim 8, wherein at least a portion of said sulfuric acid mixed with said cleavage feed in step (b) is provided by one or more of adding sulfuric acid to said cleavage feed, mixing said cleavage feed with said cleavage recycle and with sulfuric acid, adding sulfuric acid to said cleavage recycle, and adding sulfuric acid to said cleavage effluent.

11. The process of claim 8, wherein at least a portion of said phenol mixed with said cleavage feed in step (b) is provided by one or more of adding phenol to said cleavage feed, mixing said cleavage feed with said cleavage recycle and with phenol, adding phenol to said cleavage recycle, and adding phenol to said cleavage effluent.

12. The process of claim 8, wherein at least a portion of said cyclohexanone mixed with said cleavage feed in step (b) is provided by one or more of adding cyclohexanone to said cleavage feed, mixing said cleavage feed with said cleavage recycle and with cyclohexanone, adding cyclohexanone to said cleavage recycle, and adding cyclohexanone to said cleavage effluent.

13. A process for producing phenol and cyclohexanone, the process comprising:
   a. providing a cleavage feed containing cyclohexyl-1-phenyl-1-hydroperoxide;
   b. mixing said cleavage feed with at least phenol, cyclohexenone, and water to produce a cleavage reaction mixture; and
   c. reacting said cleavage reaction mixture in the presence of a sulfuric acid catalyst under conditions to maintain the weight ratio of phenol to cyclohexanone in said cleavage reaction mixture in excess of 1:1 and to convert part of said cyclohexyl-1-phenyl-1-hydroperoxide in said cleavage reaction mixture and produce a cleavage effluent containing phenol and cyclohexanone.

14. The process of claim 13, wherein said the weight ratio of phenol to cyclohexanone in said cleavage reaction mixture is from 1.05:1 to 10:1.

15. A process for producing phenol and cyclohexanone, the process comprising:
   a. hydroalkylating benzene with hydrogen in the presence of a first catalyst under conditions effective to produce a hydroalkylation product comprising cyclohexylbenzene;
   b. contacting at least part of said cyclohexylbenzene with an oxygen-containing compound in the presence of a second catalyst under oxidation conditions effective to produce an oxidation product comprising cyclohexyl-1-phenyl-1-hydroperoxide and unreacted cyclohexylbenzene;
   c. providing from said oxidation product a cleavage feed containing greater than 40 wt % and no greater than 95 wt % cyclohexyl-1-phenyl-1-hydroperoxide, and at least 5 wt % and less than 60 wt % cyclohexylbenzene;
   d. mixing said cleavage feed with at least phenol, cyclohexanone, water, and sulfuric acid, to produce a cleavage reaction mixture containing from 15 wt % to 50 wt % phenol, from 15 wt % to 50 wt % cyclohexanone, from 1 wt % to 10 wt % cyclohexyl-1-phenyl-1-hydroperoxide, from 5 wt % to 60 wt % cyclohexylbenzene, from 0.1 wt % to 4 wt % water, and from 10 wppm to 1000 wppm sulfuric acid; and
   e. reacting said cleavage reaction mixture at a temperature from 30° C. and to 70° C. for a time sufficient to convert at least 50% of said cyclohexyl-1-phenyl-1-hydroperoxide in said cleavage reaction mixture and produce a cleavage effluent containing phenol and cyclohexanone.

16. The process of claim 15, wherein said cleavage feed contains from 60 wt % to 85 wt % cyclohexyl-1-phenyl-1-hydroperoxide, and from 15 wt % to 40 wt % cyclohexylbenzene.

17. The process of claim 15, wherein said cleavage reaction mixture contains from 25 wt % to 45 wt % phenol, from 25 wt % to 45 wt % cyclohexanone, from 1 wt % to 6 wt % cyclohexyl-1-phenyl-1-hydroperoxide, from 15 wt % to 40 wt % cyclohexylbenzene, from 0.5 wt % to 3.0 wt % water, and from 20 wppm to 500 wppm sulfuric acid.

18. The process of claim 15, wherein said reacting (e) is conducted at a temperature from 40° C. to 60° C.

19. The process of claim 15, wherein said reacting (e) occurs at a cyclohexyl-1-phenyl-1-hydroperoxide rate constant from 0.1 min$^{-1}$ to 20 min$^{-1}$.

20. The process of claim 15, wherein the cleavage reaction mixture contains at least 1 wt % more phenol than the wt % of cyclohexanone.

21. The process of claim 15, further including (f) dividing said cleavage effluent into at least a cleavage product and a cleavage recycle, wherein the cleavage recycle provides at least a portion of said phenol, cyclohexanone, water, and sulfuric acid mixed with said cleavage feed in step (d).

22. The process of claim 21, wherein at least a portion of said water mixed with said cleavage feed in step (d) is provided by one or more of adding water to said cleavage feed, mixing said cleavage feed with said cleavage recycle and with water, adding water to said cleavage recycle, and adding water to said cleavage effluent.

23. The process of claim 21, wherein at least a portion of said sulfuric acid mixed with said cleavage feed in step (d) is provided by one or more of adding sulfuric acid to said cleavage feed, mixing said cleavage feed with said cleavage recycle and with sulfuric acid, adding sulfuric acid to said cleavage recycle, and adding sulfuric acid to said cleavage effluent.

24. The process of claim 21, wherein at least a portion of said phenol mixed with said cleavage feed in step (d) is provided by one or more of adding phenol to said cleavage feed, mixing said cleavage feed with said cleavage recycle and with phenol, adding phenol to said cleavage recycle, and adding phenol to said cleavage effluent.

25. The process of claim 21, wherein at least a portion of said cyclohexanone mixed with said cleavage feed in step (d) is provided by one or more of adding cyclohexanone to said cleavage feed, mixing said cleavage feed with said cleavage recycle and with cyclohexanone, adding cyclohexanone to said cleavage recycle, and adding cyclohexanone to said cleavage effluent.

* * * * *